United States Patent [19]

Miller

[11] 4,371,494

[45] Feb. 1, 1983

[54] METHOD FOR MANUFACTURING A THERMOPLASTIC CYLINDRICAL CLAMP

[75] Inventor: Jack V. Miller, Sierra Madre, Calif.

[73] Assignee: Gravity Guidance, Incorporated, Pasadena, Calif.

[21] Appl. No.: 203,336

[22] Filed: Nov. 3, 1980

[51] Int. Cl.³ .............................................. B29C 17/04
[52] U.S. Cl. ..................................... 264/522; 29/463; 264/545; 264/554; 264/295; 264/296
[58] Field of Search ............... 264/522, 544, 545, 554, 264/295, 296, 138, 292; 29/428, 463

[56] References Cited

U.S. PATENT DOCUMENTS

| | | | |
|---|---|---|---|
| 3,489,265 | 1/1970 | Puente | 264/295 X |
| 3,767,752 | 10/1973 | Karlyn et al. | 264/295 X |
| 3,960,181 | 6/1976 | Baur et al. | 138/178 |
| 4,002,417 | 1/1977 | Vecchiotti et al. | 264/296 X |

Primary Examiner—Jan H. Silbaugh
Attorney, Agent, or Firm—Zarley, McKee, Thomte, Voorhees & Sease

[57] ABSTRACT

A thermoplastic cylindrical clamp is manufactured by heating a flat sheet of thermoplastic material, thermoforming the softened sheet over a mold having two parallel and semicylindrical shapes with a narrow planar space between them and a coplanar flange surrounding, trimming the thermoformed sheet so the semicylinders are open at each end, locally heating the narrow planar portion between the semicylinders to the softening point, bending the softened portion so the semicylinders form a complete cylinder and cooling the part in the cylindrical shape.

4 Claims, 5 Drawing Figures

METHOD FOR MANUFACTURING A THERMOPLASTIC CYLINDRICAL CLAMP

BACKGROUND OF THE INVENTION

This invention relates to the manufacture of a device for clamping a generally cylindrical object, using plastic thermoforming processes, and more specifically to the low cost manufacture of clamping devices that conform closely to human limbs to provide support for various forms of traction therepy. Such clamping devices are known, and one is described in U.S. Pat. No. 3,380,447 (Martin), in which a cylindrical clamping device is made of metal, and is used for supporting a human in inverted posture by clamping the ankles and suspending the clamps from a horizontal bar by means of hooks.

The variety of sizes and forms of human limbs, through the range from children to large adults, makes it desireable to make traction clamps through a process employing simple, low cost tooling. Plastic thermoforming is well known for this advantage, and hence is found in use for making a variety of splints and body casts that are fitted to individual patients, using inexpensive molds. Although human limbs are generally cylindrical, clamping devices for traction should be shaped as closely as possible to the contour of the limb so that padding within the clamp provides the most uniform unit pressure possible to the skin of the patient.

The natural flexibility of plastics normally used for thermoforming helps the clamp to conform anatomically to the limb. However, thermoforming is limited to shapes that have little or no negative draft on the mold; meaning that a cylindrical object, such as a clamp cannot be directly formed by that process. Therefore a secondary forming operation is necessary to form a complete cylinder.

Local heating and bending is well known in the plastics industry, and is commonly referred to as "hot-wire" bending. In this process a flat sheet of plastic is placed over a hot electrical resistance wire until the localized radiant heating softens the plastic sheet along the intended bend line. A bend is made, and the plastic is cooled in the bent configuration.

Local stretch-thinning is also well known, and is shown by my U.S. Pat. No. 3,760,178 which teaches the use of thermoforming to intentionally thin a plastic web. Stretch-thinning of plastic for the purpose of providing a flexural hinge line is shown in my co-pending application Ser. No. 06/142,673 entitled Thermoformed Plastic Hinge.

SUMMARY OF THE INVENTION

According to the invention a thermoplastic cylindrical clamp is manufactured by heating a flat sheet of thermoplastic material to the softenting point, thermoforming the softened plastic sheet over a mold having two semicylindrical shapes in a parallel relationship and spaced apart by a narrow planar portion, and having a surrounding coplanar flange. After forming the sheet is trimmed so the ends of the of the semicylinders are open. Then localized heat is applied to the planar portion between the semicylinders to re-soften the plastic, and the plastic is bent 180° so the extreme flanges are juxtaposed and the semicylinders form a complete cylinder prior to cooling In a preferred embodiment the material in the area of the narrow planar portion is stretch-thinned by the thermoforming process, facilitating the secondary heat bending procedure, and providing a somewhat flexible area for opening and closing the clamp. Another preferred embodiment has the juxtaposed flanges trimmed into the shape of a hook, whereby the clamp, and the limb being clamped, may be suspended from a bar means. Still another embodiment provides a fastening means attached permanently to one of the semicylinders and temporarily to the other semicylinder, whereby the fastening means locks the clamp together in the cylindrical form with the flanges juxtaposed.

DETAILED DESCRIPTION OF THE DRAWINGS

Figure 1:
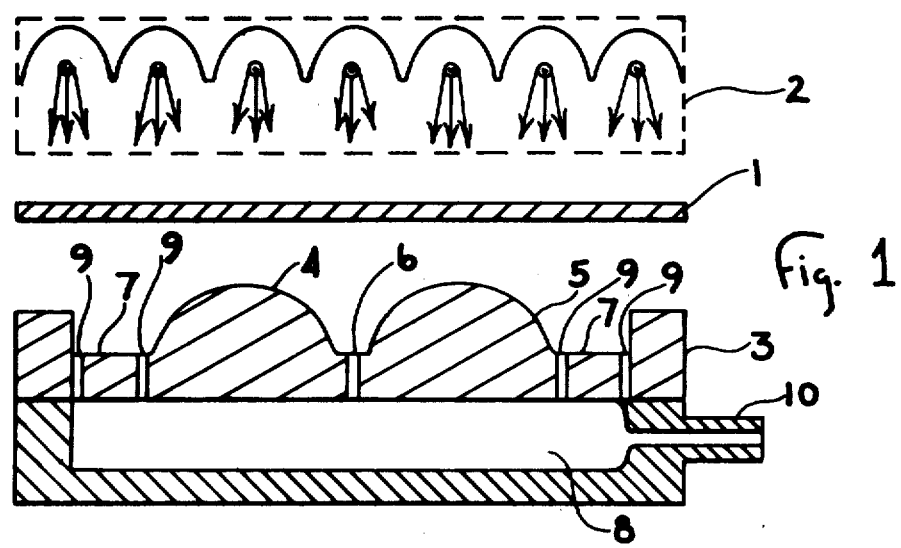
FIG. 1 is a cross sectional elevation view showing a sheet of thermoplastic above a thermoforming mold according to the invention.

In FIG. 1 a sheet of thermoplastic material 1 is shown being heated by a heat source 2 over a mold 3 which is provided with two semicylindrical shapes 4 and 5 with a narrow planar space 6 between the semicylindrical shapes and a coplanar flange 7 surrounding the semicylinders. Mold 3 is provided with a vacuum plenum 8 which is vented to the mold surface by a plurality of small holes 9, and plenum 8 is also connected to an outlet 10.

Figure 2:
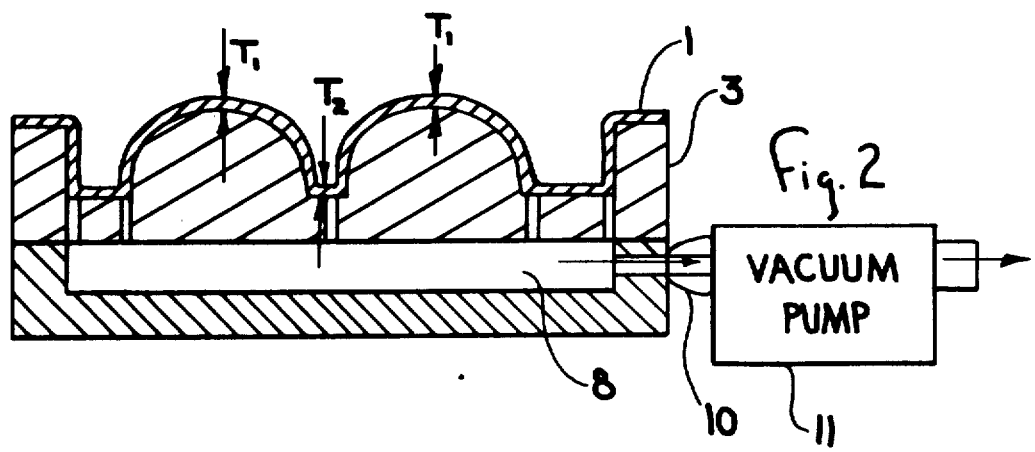
FIG. 2 is a cross sectional elevation view of the mold of FIG. 1 and showing the plastic sheet formed to the mold.

In FIG. 2 the heated sheet 1 is shown formed into the contour of mold 3 by the application of vacuum to plenum 8 by a vacuum pump 11 which is connected to outlet 10. Without any continued application of heat to sheet 1 it freezes in the contour of mold 3, with a thickness $T_1$ existing where sheet 1 is not subject to stretching during forming and thereby $T_1$ is approximately the original unformed thickness of sheet 1. Where stretching of sheet 1 is caused by forming the sheet into the planar space 6, thickness $T_2$ is produced which is substanitally thinner than $T_1$.

Figure 3:
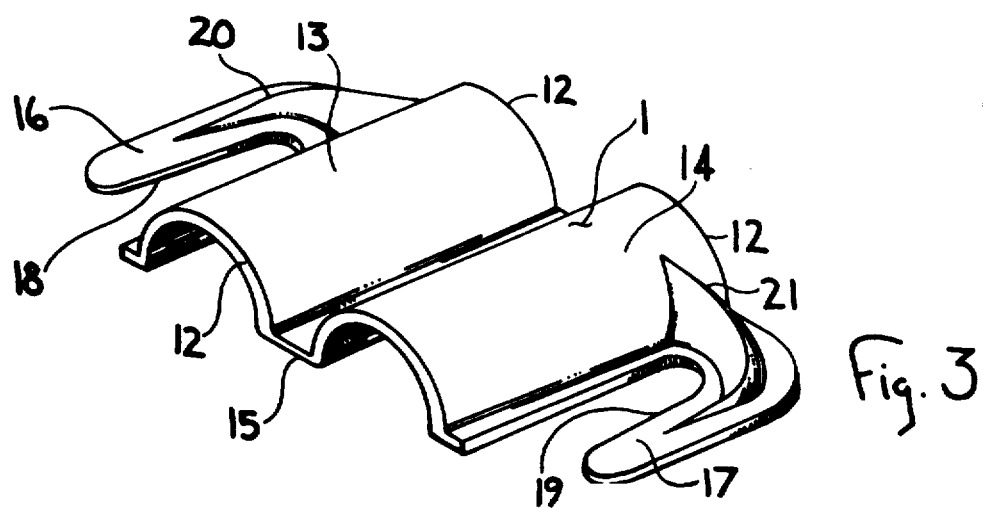
FIG. 3 is a perspective view of the thermoformed sheet shown after trimming.

FIG. 3 shows sheet 1 removed from the mold and trimmed so that the semicircular ends 12 are open, and hollow semicylinders 13 and 14 are contiguous with a bridge 15. Coplanar flanges 16 and 17 are trimmed into the shape of mirror-image hooks 18 and 19 which are stiffened by integrally formed ribs 20 and 21.

Figure 4:
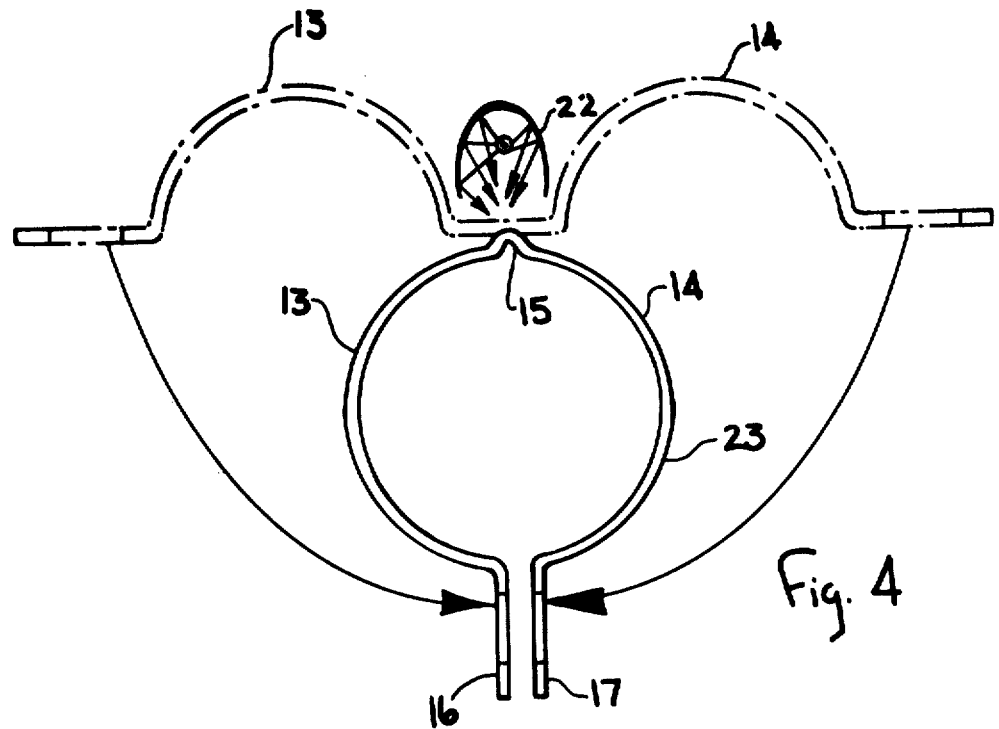
FIG. 4 is a cross sectional view of the trimmed sheet being closed to a cylindrical configuration.

In FIG. 4 a linear, narrow heat source 22 is shown applied to the bridge 15 between semicylinders 13 and 14, thereby softening bridge 15 sufficiently to bring flanges 16 and 17 into juxtaposition, wherein semicylinders 13 and 14 form a complete cylinderical clamp 23.

Figure 5:
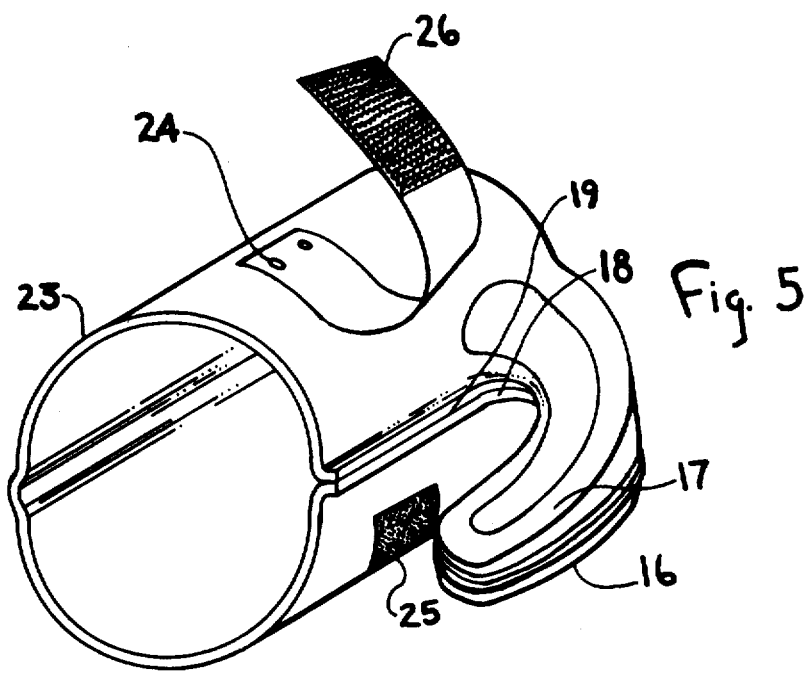
FIG. 5 is a perspective view of the completed clamp according to the invention.

In FIG. 5 clamp 23 is shown with hooks 18 and 19 congruent and flanges 16 and 17 juxtaposed. A locking means 24 is shown in an unlocked condition and has a hook means 25 engageable with a latch means 26 to hold flanges 16 and 17 in abuttment.

The foregoing specification discloses the technique for manufacturing a generally cylindrical thermoplastic clamp in a manner that is inexpensively tooled and produced. Therefore the process has great versatility with respect to the objects to be clamped, and is well suited to adaptation to objects of irregular shape, human limbs, animate objects, as well as inanimate objects within the intended scope of the invention.

The simplest embodiments are shown in the interest of clarity, and such features as the locking means and flange shapes may be varied substantially within the scope of the invention.

I claim:

1. A method for manufacturing a thermoplastic open ended cylindrical clamp including the following steps:

heating a flat sheet of thermoplastic material to its softening point;

providing a mold having two semicylindrical shapes in a parallel relationship with a narrow planar surface therebetween and a coplanar flange surrounding the semicylinders, said planar surface being sufficiently narrow that plastic thermoformed over the mold will be locally stretch-thinned at said planar surface to a thickness no greater than 60% of the original sheet thickness;

thermoforming the softened plastic sheet over the mold thereby forming a pair of spaced apart semicylindrical portions connected together by a thinned planar portion positioned therebetween and each having an extreme flange along one side thereof;

trimming the sheet to a form wherein the semicylindrical portions are open at each end;

applying sufficient localized heat to the planar portion between the semicylindrical portions to re-soften the plastic;

bending the locally re-softened planar portion approximately 180° so the extreme flanges along one side of semicylindrical portion are juxtaposed as the semicylindrical portions form a complete cylinder; and cooling the plastic part in the cylindrical shape suitable for clamping a generally cylindrical object therein, said trimming step including trimming each said extreme flange in the shape of a hook so configured as to permit suspension of the clamp and an object clamped therein from a bar, said thermoforming step including thermoforming a stiffening rib as a projection from each semicylindrical portion substantially through the length of the portion of the juxtaposed flange to be trimmed in the shape of a hook.

2. A method for manufacturing a thermoplastic cylindrical clamp as in claim 1 in which the locally heated plastic portion between the semicylinders is bent more than 180° and is cooled to retain a compressive force between the juxtaposed flanges.

3. A method for manufacturing a thermoplastic cylindrical clamp as in claim 1 in which the locally heated plastic portion between the semicylinders is bent less that 180° and is cooled with a space between the juxtaposed flanges.

4. A method for manufacturing a thermoplastic cylindrical clamp as in claim 1 in which a locking means is attached to the semicylinders whereby the juxtaposed flanges are held in abuttment.

* * * * *